US007917372B2

(12) United States Patent
Oscar et al.

(10) Patent No.: US 7,917,372 B2
(45) Date of Patent: Mar. 29, 2011

(54) PHARMACY BENEFITS MANAGEMENT METHOD AND APPARATUS

(75) Inventors: Robert S Oscar, Richmond, VA (US); John E Dietz, Richmond, VA (US); Bryan W York, Mechanicsville, VA (US); Dean T Ousterhout, Williamsburg, VA (US); Rob Hauser, Richmond, VA (US); Matthew Rokenbrod, Richmond, VA (US); Ilia Brusilovsky, Richmond, VA (US)

(73) Assignee: RXEOB/COM.LLC, Richmond, VA (US)

( * ) Notice: Subject to any disclaimer, the term of this patent is extended or adjusted under 35 U.S.C. 154(b) by 2761 days.

(21) Appl. No.: 09/811,769

(22) Filed: Mar. 20, 2001

(65) Prior Publication Data
US 2001/0037216 A1 Nov. 1, 2001

Related U.S. Application Data

(60) Provisional application No. 60/190,556, filed on Mar. 20, 2000.

(51) Int. Cl.
*G06Q 50/00* (2006.01)
*G06Q 40/00* (2006.01)
(52) U.S. Cl. ............................................. 705/2; 705/4
(58) Field of Classification Search .................... 705/2, 3
See application file for complete search history.

(56) References Cited

U.S. PATENT DOCUMENTS

| 4,837,693 | A | | 6/1989 | Schotz |
| 4,916,611 | A | | 4/1990 | Doyle, Jr. et al. |
| 5,235,507 | A | | 8/1993 | Sackler et al. |
| 5,301,105 | A | | 4/1994 | Cummings, Jr. |
| 5,519,607 | A | | 5/1996 | Tawil |
| 5,737,539 | A | | 4/1998 | Edelson et al. |
| 5,758,095 | A | | 5/1998 | Albaum et al. |
| 5,832,449 | A | | 11/1998 | Cunningham |
| 5,845,255 | A | * | 12/1998 | Mayaud ............................ 705/3 |
| 5,935,704 | A | | 8/1999 | Happy |
| 5,970,462 | A | | 10/1999 | Reichert |
| 5,970,463 | A | | 10/1999 | Cave et al. |
| 5,991,731 | A | | 11/1999 | Colon et al. |
| 6,000,828 | A | | 12/1999 | Leet |
| 6,012,035 | A | | 1/2000 | Freeman, Jr. et al. |
| 6,014,631 | A | | 1/2000 | Teagarden et al. |
| 6,195,612 | B1 | * | 2/2001 | Pack-Harris ....................... 702/2 |
| 6,947,900 | B2 | * | 9/2005 | Giordano et al. ............... 705/26 |
| 2002/0049617 | A1 | * | 4/2002 | Lencki et al. ..................... 705/4 |
| 2009/0089392 | A1 | * | 4/2009 | Fiedotin et al. ............... 709/207 |

OTHER PUBLICATIONS

Mott, David A.; Kreling, David H., "The Association of Insurance Type with Cost of Dispensed Drugs," Spring 1998, Inquiry-Blue Cross and Blue Shield Assoc., vol. 35 No. 1, pp. 23-35.*

* cited by examiner

*Primary Examiner* — C. Luke Gilligan
*Assistant Examiner* — Rachel L Porter
(74) *Attorney, Agent, or Firm* — Marc S. Kaufman; Nixon Peabody, LLP

(57) ABSTRACT

A pharmacy benefits management system and method. A processor server has claim information relating to pharmacy benefits claims, and information relating to a claims processing formularly stored therein. A provider server has pharmacy benefits plan structure information stored therein. A management server has price information relating drugs in various classes and a processing module for correlating the claim information with the benefits plan structure information and the formularly information to identify drugs dispensed to patients, expenses associated with the drugs in accordance with the pharmacy benefits plan structure information, alternative drugs in the same class as the drugs and expenses associated with the alternative drugs.

25 Claims, 24 Drawing Sheets

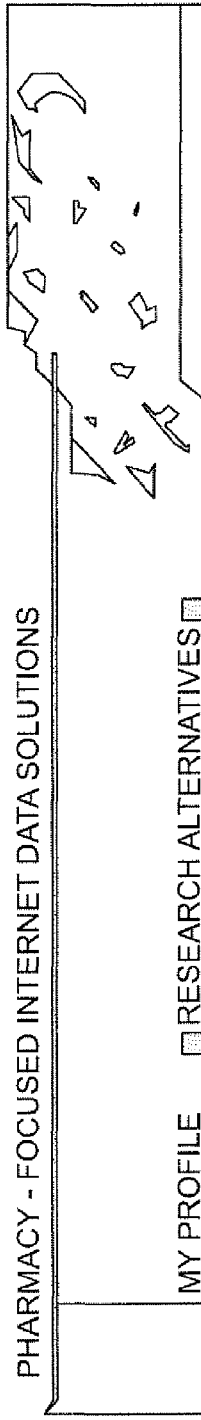

PHARMACY - FOCUSED INTERNET DATA SOLUTIONS

MY PROFILE | RESEARCH ALTERNATIVES

REGISTRATION (STEP 1)

ENTER THE FIRST FEW LETTERS OF YOUR COMPANY'S NAME.

222 [SA]   224 [CONTINUE]

INSTRUCTIONS:
- PLEASE NOTE: IF YOU ALREADY HAVE A LOGON ID AND PASSWORD AND KNOW WHAT THEY ARE, PLEASE DO NOT REGISTER.
- PUBLIC EMPLOYEES MAY BE LISTED UNDER COUNTY OR CITY FIRST. e.g. COUNTY OF HENRICO, COUNTY SCHOOL BOARD OF HENRICO
- THIS IS THE BEGINNING OF THE REGISTRATION PROCESS. PLEASE ENTER AT LEAST THE FIRST TWO LETTERS OF YOUR EMPLOYER'S NAME INTO THE BOX ABOVE AND CLICK THE "CONTINUE" BUTTON.
- A LIST OF COMPANIES WHOSE NAMES START WITH THOSE CHARACTERS WILL APPEAR. YOU WILL THEN SELECT YOUR EMPLOYER FROM THAT LIST.

HOME | TERMS OF USE | PRIVACY POLICY | OUR COMMITMENT | INTERNET SECURITY | CONTACT US

© 2000-2001 RxEOB.COM, PHARMACY-FOCUSED DATA SOLUTIONS, ALL RIGHTS RESERVED.

*FIG. 3*

PHARMACY - FOCUSED INTERNET DATA SOLUTIONS

| MY PROFILE | ☐ RESEARCH ALTERNATIVES ☐ |

REGISTRATION (STEP 2)

PLEASE FIND BELOW OUR LIST OF EMPLOYERS THAT START WITH 'SA'.

CLICK ON YOUR COMPANY TO CONTINUE; HOWEVER, IF YOU DON'T FIND YOUR COMPANY IN THE LIST, CLICK HERE TO TRY AGAIN.

COMPANY NAME —— 226  CITY —— 228

SAMPLE COMPANY 1                    MANASSAS
SAMPLE CONSULTING CONSORTIUM        RICHMOND
SAMPLE EMPLOYER 1                   RICHMOND
SAMPLE EMPLOYER 2                   RICHMOND
SAMPLE EMPLOYER 3                   RICHMOND
SAMPLE EMPLOYER 4                   RICHMOND
SAMPLE EMPLOYER 5                   RICHMOND

HOME | TERMS OF USE | PRIVACY POLICY | OUR COMMITMENT | INTERNET SECURITY | CONTACT US

© 2000-2001 RxEOB.COM, PHARMACY-FOCUSED DATA SOLUTIONS, ALL RIGHTS RESERVED.

*FIG. 4*

PHARMACY - FOCUSED INTERNET DATA SOLUTIONS

MY PROFILE ☐ RESEARCH ALTERNATIVES ☐

REGISTRATION (STEP 3)

PLEASE ENTER THE FOLLOWING INFORMATION FROM YOUR HEALTHCARE INSURANCE CARD.

SUBSCRIBER (CARDHOLDER) INFORMATION

SUBSCRIBER'S LAST NAME: [_____] 232
MEMBER NUMBER: [_____] 234
NOTE: USE THE 9 DIGITS AFTER THE DASH.

MEMBER (DEPENDENT) INFORMATION

MEMBER'S FIRST NAME: [_____] 236
MEMBER'S LAST NAME: [_____] 238
MEMBER'S DATE OF BIRTH: [_____] (04/25/1955, MM/DD/YYYY)
MEMBER'S PERSON CD: [▼] 242
244 — NOTE: THIS IS THE '00' '01'...ON THE SAME LINE AS YOUR NAME. DATE OF BIRTH IS FOR THE MEMBER WHOSE PERSON CD YOU SELECTED.

MEMBER'S EMAIL ADDRESS: [_____] 246
YOUR EMAIL ADDRESS WILL ENABLE RxEOB TO PROVIDE YOU WITH TIMELY CUSTOMIZED INFORMATION ABOUT YOUR PHARMACY BENEFIT PLAN.

[ CONTINUE ] 248

HOME | TERMS OF USE | PRIVACY POLICY | OUR COMMITMENT | INTERNET SECURITY | CONTACT US

© 2000-2001 RxEOB.COM, PHARMACY-FOCUSED DATA SOLUTIONS, ALL RIGHTS RESERVED.
LAST MODIFIED: 02/26/2001, VERSION 3.3.5

*FIG. 5*

HOME  DRUG LOOKUP  Rx HISTORY  HELP  DEPENDENTS

PLAN MEMBER

MY PROFILE ☐ RESEARCH ALTERNATIVES ☐

WHO ELSE IN MY FAMILY CAN VIEW MY DATA?

CURRENT AUTHORIZATION STATUS

| DEPENDENT CODE | DATE OF BIRTH | AUTHORIZATION |
|---|---|---|
| 1 | 01/01/1948 | AUTHORIZED |
| 2 | 01/01/1979 | NOT AUTHORIZED |
| 3 | 01/01/1992 | NOT AUTHORIZED |

— 252

CHANGE AUTHORIZATION FOR FAMILY MEMBER

| DEPENDENT CODE | AUTHORIZATION DESCRIPTION |
|---|---|
| 254 — ☐▼ | ▼ — 256 |

[CHANGE AUTHORIZATION]

HOME | DRUG LOOKUP | HELP | MY PROFILE | RESEARCH | DEPENDENTS
TERMS OF USE | PRIVACY POLICY | OUR COMMITMENT | INTERNET SECURITY | CONTACT US
© 2000-2001 RxEOB.COM, PHARMACY-FOCUSED DATA SOLUTIONS, ALL RIGHTS RESERVED.

*FIG. 6*

HOME  DRUG LOOKUP  RX HISTORY  HELP  DEPENDENTS

PLAN MEMBER

MY PROFILE  ☐ RESEARCH ALTERNATIVES ☐

RESEARCH ALTERNATIVES

TO RESEARCH THE AVAILABILITY AND COST OF THE THERAPEUTIC ALTERNATIVES TO THE DRUGS YOU ARE CURRENTLY TAKING, PLEASE SELECT THE DRUG YOU WISH TO RESEARCH FROM THE DROP DOWN LIST LOCATED BELOW.

DRUG CHOICES: [SELECT DRUG HERE ▼] ~ 282
ENTER QUANTITY: [   ] (SEE INSTRUCTIONS BELOW)
284 ⌐ [CONTINUE] ~ 286

IF YOU WISH TO RESEARCH DRUGS OTHER THAN THOSE YOU ARE CURRENTLY TAKING, CLICK HERE TO GO TO OUR DRUG LOOKUP FUNCTION.

INSTRUCTIONS FOR ENTERING QUANTITY INFORMATION:

- WITH TABLETS, CAPSULES, OR SUPPOSITORIES, ENTER THE NUMBER INDICATED ON YOUR PRESCRIPTION LABEL.
- WITH LIQUIDS, ENTER THE NUMBER OF CC'S OR ML'S INDICATED ON YOUR PRESCRIPTION LABEL.
- WITH TOPICALS OR INHALERS, ENTER THE NUMBER OF GRAMS INDICATED ON YOUR PRESCRIPTION LABEL.

HOME | DRUG LOOKUP | HELP | MY PROFILE | RESEARCH | DEPENDENTS
TERMS OF USE | PRIVACY POLICY | OUR COMMITMENT | INTERNET SECURITY | CONTACT US
© 2000-2001 RxEOB.COM, PHARMACY-FOCUSED DATA SOLUTIONS, ALL RIGHTS RESERVED.

*FIG. 9*

HOME   DRUG LOOKUP   MY HISTORY   HELP   DEPENDENTS

PLAN MEMBER

MY PROFILE  ☐ RESEARCH ALTERNATIVES ☐

THERAPEUTIC ALTERNATIVES

DRUG NAME:    ACIPHEX 20 MG TABLET EC
DRUG CLASS:   PROTON PUMP INHIBITORS

DRUG QUANTITY: 30

| DRUG NAME | ESTIMATED RETAIL PRICE PRESCRIPTION COST | RETAIL COPAY (31 DAYS) | MAIL ORDER COPAY (31 DAYS) |
|---|---|---|---|
| • PROTONIX 40 MG TABLET EC | $75.00 | $25 | $50 |
| PREVACID 15 MG CAPSULE DR | $98.04 | $25 | $50 |
| • PREVACID 30 MG CAPSULE DR | $99.91 | $25 | $50 |
| PRILOSEC 10 MG CAPSULE DR | $111.25 | $10 | $20 |
| ACIPHEX 20 MG TABLET EC | $113.98 | $25 | $50 |
| • PRILOSEC 20 MG CAPSULE DR | $124.18 | $10 | $20 |
| PRILOSEC 40 MG CAPSULE DR | $178.20 | $10 | $20 |

PLEASE NOTE: WHEN COST OF A PRESCRIPTION DRUG IS LESS THAN THE PROJECTED COPAY, MOST BENEFIT PLANS REQUIRE YOU PAY ONLY THE COST OF THE DRUG. THE TERMS OF YOUR PRESCRIPTION BENEFIT ARE SUBJECT TO CHANGE. CONTACT YOUR PLAN SPONSOR FOR MORE INFORMATION.

THIS INFORMATION IS DESIGNED TO FACILLITATE COMMUNICATION BETWEEN YOU AND YOUR DOCTOR. WHILE DRUGS IN THIS LIST CAN BE ALTERNATIVES FOR ONE ANOTHER, YOUR SPECIFIC DOSAGE REQUIREMENTS MUST BE DETERMINED BY YOUR DOCTOR. RxEOB.COM IS NOT RECOMMENDING THAT YOU CHANGE YOUR DRUG THERAPY.

HOME | DRUG LOOKUP | HELP | MY PROFILE | RESEARCH | DEPENDENTS
TERMS OF USE | PRIVACY POLICY | OUR COMMITMENT | INTERNET SECURITY | CONTACT US
© 2000-2001 RxEOB.COM, PHARMACY-FOCUSED DATA SOLUTIONS, ALL RIGHTS RESERVED.

FIG. 10A

FIG. 10B

| DRUG NAME | ESTIMATED RETAIL PRICE PRESCRIPTION COST | RETAIL COPAY FOR UP TO 31 DAYS SUPPLY | MAIL ORDER COPAY FOR UP TO 91 DAYS SUPPLY |
|---|---|---|---|
| LOTENSIN 5MG TABLET | $27.00 | $25 | $50 |
| ZESTRIL 5MG TABLET | $28.01 | $25 | $50 |
| ZESTRIL 10MG TABLET | $28.94 | $25 | $50 |
| ACEON 2 MG TABLET | $30.42 | $25 | $50 |
| ACEON 4 MG TABLET | $30.42 | $25 | $50 |
| ALTACE 2.5 MG CAPSULE | $30.59 | $10 | $20 |
| CAPOTEIN 25MG TABLET | $30.68 | $25 | $50 |
| PRINIVIL 20MG TABLET | $30.97 | $10 | $20 |
| ZESTRIL 20MG TABLET | $30.97 | $25 | $50 |
| ACCUPRIL 10MG TABLET | $31.47 | $10 | $20 |
| ACCUPRIL 20MG TABLET | $31.47 | $10 | $20 |
| ACCUPRIL 40MG TABLET | $31.47 | $10 | $20 |
| ACCUPRIL 5MG TABLET | $31.47 | $10 | $20 |
| ENALAPRIL MALLATE 20MG TAB | $32.26 | $5 | $10 |
| ALTACE 5MG CAPSULE | $33.40 | $10 | $20 |
| VASOTEC 5MG TABLET | $35.45 | $25 | $50 |
| VASOTEC 10MG TABLET | $37.15 | $25 | $50 |
| PRINIVIL 40MG TABLET | $37.74 | $10 | $20 |
| ALTACE 10MG CAPSULE | $39.43 | $10 | $20 |
| VASOTEC 20MG TABLET | $41.81 | $25 | $50 |
| ACEON 8MG TABLET | $43.68 | $25 | $50 |
| ZESTRIL 30MG TABLET | $43.84 | $25 | $50 |
| LAPOTEN 50MG TABLET | $44.31 | $25 | $50 |
| ZESTRIL 40MG TABLET | $45.29 | $25 | $50 |
| CAPOTEN 100MG TABLET | $59.01 | $25 | $50 |

PLEASE NOTE: WHEN THE COST OF A PRESCRIPTION DRUG IS LESS THAN THE PROJECTED COPAY, MOST BENEFIT PLANS REQUIRE YOU PAY ONLY THE COST OF THE DRUG. THE TERMS OF YOUR PRESCRIPTION BENEFIT ARE SUBJECT TO CHANGE. CONTACT YOUR PLAN SPONSOR FOR MORE INFORMATION.
THIS INFORMATION IS DESIGNED TO FACILITATE COMMUNICATION BETWEEN YOU AND YOUR DOCTOR. WHILE DRUGS IN THIS LIST CAN BE ALTERNATIVES FOR ONE ANOTHER, YOUR SPECIFIC DOSAGE REQUIREMENTS MUST BE DETERMINED BY YOUR DOCTOR. RxEOB.COM IS NOT RECOMMENDING THAT YOU CHANGE YOUR DRUG THERAPY.

HOME DRUG LOOKUP Rx HISTORY HELP

PLAN SPONSOR

MY PROFILE ☐ RESEARCH ALTERNATIVES ☐ PLAN SPONSOR

PLAN SPONSOR REPORTS

REPORT DATE RANGE:

START DATE: [1999-12-31] (306) END DATE: [1999-12-31] (308) (1999-01-24)(YYYY-(MM-DD)

DRUG UTILIZATION STATISTICS:

310 — ⦿ AGGREGATED BY DRUG CLASS (WITH "DRILL-DOWN" CAPABILITY TO LIST DRUGS WITHIN EACH CLASS)

PRESCRIPTION CLAIMS AND AUDIT REPORTS:

PLEASE SELECT ONE OR MORE OF THE REPORTS LISTED BELOW. MULTIPLE REPORTS CAN BE ACCESSED AT THE SAME TIME.

312 — 
- ○ TOTAL CLAIMS AND RELATED COSTS
- ○ VERIFIED CLAIMS AND RELATED COSTS
- ○ COMPARISON OF TOTAL TO VERIFIED CLAIMS
- ○ CLAIMS FAILING VERIFICATION AND RELATED COSTS
- ○ REASONS FOR CLAIMS FAILING VERIFICATION
- ○ CLAIM VERIFICATION RESPONSE DISTRIBUTION
- ○ CLAIMS DISTRIBUTION BY MONTH

314

HOME | DRUG LOOKUP | HELP | MY PROFILE | RESEARCH | DEPENDENTS
TERMS OF USE | PRIVACY POLICY | OUR COMMITMENT | INTERNET SECURITY | CONTACT US
© 2000-2001 RxEOB.COM, PHARMACY-FOCUSED DATA SOLUTIONS, ALL RIGHTS RESERVED.
LAST MODIFIED: 02/26/2001, VERSION 3.3.5

FIG. 12

HOME  DRUG LOOKUP  Rx HISTORY  HELP

PLAN SPONSOR

MY PROFILE  ☐ RESEARCH ALTERNATIVES  ☐ PLAN SPONSOR

PLAN SPONSOR VIEW REPORTS
EMPLOYER:   SAMPLE EMPLOYER 1
DRUG UTILIZATION GROUPED BY DRUG CLASS FOR 12/31/1999 THROUGH 12/31/2001

| DRUG CLASS | PLAN PAYMENT | PLAN % OF TOTAL | PATIENT TOTAL | PATIENT % OF TOTAL |
|---|---|---|---|---|
| SELECTIVE SEROTONIN REUPTAKE INHIBITORS | $23,554.92 | 9.60% | $3,785.00 | 4.66% |
| HMG COA REDUCTASE INHIBITORS | $15,870.43 | 6.47% | $2,760.00 | 3.40% |
| OTHER ANTIHISTAMINES NONSEDATING | $15,599.86 | 6.36% | $3,300.00 | 4.06% |
| PROTON PUMP INHIBITORS | $11,183.93 | 4.56% | $1,625.00 | 2.00% |
| SERATONIN (SHT3) ANTAGONISTS | $9,420.76 | 3.84% | $285.00 | .35% |
| OTHER ANTIDEPRESSANTS | $9,039.88 | 3.68% | $1,419.44 | 1.74% |
| OTHER ANTIEPILEPTICS | $6,981.92 | 2.84% | $500.00 | .61% |
| CORTICOSTEROIDS | $6,562.64 | 2.67% | $3,144.14 | 3.87% |
| OTHER ANTIHISTAMINES, NONSEDATING COMBINATIONS | $6,468.44 | 2.63% | $1,920.00 | 2.36% |
| PROGESTOGENS AND ESTROGENS, SEQUENTIAL PREPARATION | $5,145.66 | 2.09% | $3,614.46 | 4.45% |
| FLOUROQUINOLONES | $5,031.32 | 2.05% | $944.99 | 1.16% |
| INTERFERONS | $5,008.44 | 2.04% | $60.00 | .07% |
| SYMPATHOMIMETIC COMBINATIONS | $4,386.51 | 1.78% | $1,460.00 | 1.79% |
| COMBINATIONS OF PENECILLINS, INCL. BETA-LACTAMASE | $4,383.64 | 1.78% | $834.04 | 1.00% |
| AMINOSALICYLIC ACID AND SIMILAR AGENTS | $4,151.50 | 1.69% | $450.00 | .55% |
| MACROLIDES | $4,103.55 | 1.67% | $1,285.60 | 1.58% |
| SELECTIVE SHT1-RECEPTOR AGONISTS | $3,977.58 | 1.62% | $510.00 | .67% |

*FIG. 13*

HOME DRUG LOOKUP Rx HISTORY HELP

PLAN SPONSOR

MY PROFILE ☐ RESEARCH ALTERNATIVES ☐ PLAN SPONSOR

DRUG USAGE REPORT - INDIVIDUAL DRUG WITHIN DRUG CLASS — 336

IF YOU WOULD LIKE TO SEE HOW YOUR FORMULARY TREATS THIS DRUG CLASS, ENTER THE APPROPRIATE QUANTITY AND CLICK THE BUTTON.

ENTER QUANTITY: [____] (NUMBERS ONLY)

DRUG CLASS: — 328 — SELECTIVE SEROTONIN REUPTAKE INHIBITORS

| BRAND NAME | PLAN EXPENSE | PLAN PERCENT OF TOTAL | RECIPIENT EXPENSE | RECIPIENT % OF TOTAL |
|---|---|---|---|---|
| PROZAC | $11,627.49 | 4.74% | $1,470.00 | 1.81% |
| PAXIL | $6,306.15 | 2.57% | $1,045.00 | 1.28% |
| ZOLOFT | $3,826.37 | 1.56% | $790.00 | .97% |
| CELEXA | $1,372.53 | .55% | $380.00 | .46% |
| LUVOX | $422.38 | .17% | $100.00 | .12% |
| TOTAL ALL CLAIMS | $245,129.99 | | $81,173.02 | |

HOME | DRUG LOOKUP | HELP | MY PROFILE | RESEARCH | DEPENDENTS | PLAN SPONSOR
TERMS OF USE | PRIVACY POLICY | OUR COMMITMENT | INTERNET SECURITY | CONTACT US
© 2000-2001 RxEOB.COM, PHARMACY-FOCUSED DATA SOLUTIONS, ALL RIGHTS RESERVED.

*FIG. 14*

HOME  DRUG LOOKUP  Rx HISTORY  HELP

PLAN SPONSOR

MY PROFILE  ☐ RESEARCH ALTERNATIVES ☐ PLAN SPONSOR

THERAPEUTIC ALTERNATIVES
DRUG CLASS:    SELECTIVE SEROTONIN REUPTAKE INHIBITORS
DRUG QUANTITY: 1

PLEASE PRINT THIS PAGE AND SHARE THE INFORMATION WITH YOUR DOCTOR. PLEASE BE AWARE THAT SOME OF THESE THERAPEUTIC ALTERNATIVES MAY NOT BE APPROPRIATE FOR YOU.

| DRUG NAME | AVERAGE RETAIL PRICE PRESCRIPTION COST | RECIPIENT COST |
|---|---|---|
| CELEXA 10MG/5ML SOLUTION | $0.41 | $10 |
| ZOLOFT 20MG/ML ORAL CONC | $0.77 | $10 |
| PROZAC 20MG/5ML SOLUTION | $1.05 | $10 |
| ZOLOFT 35MG TABLET | $1.87 | $10 |
| ZOLOFT 50MG TABLET | $1.93 | $10 |
| ZOLOFT 100MG TABLET | $1.98 | $10 |
| CELEXA 20MG TABLET | $2.16 | $10 |
| FLUVOXAMINE MALEATE 25MG TB | $2.18 | $5 |
| CELEXA 40MG TABLET | $2.25 | $10 |
| PAXIL 10MG TABLET | $2.42 | $10 |
| FLUVOXAMINE MALEATE 50MG TB | $2.44 | $5 |
| FLUVOXAMINE MAL 100MG TAB | $2.50 | $5 |
| PROZAC 10MG TABLET | $2.77 | $10 |
| SARAFEM 10MG PULVULE | $2.77 | $10 |
| PROZAC 10MG PULVUL | $2.81 | $10 |
| SARAFEM 20MG PULVULE | $2.85 | $10 |
| PROZAC 20MG PULVUL | $2.88 | $10 |
| LUVOX 25MG TABLET | $2.94 | $25 |
| LUVOX 50MG TABLET | $3.29 | $25 |
| LUVOX 100MG TABLET | $3.37 | $25 |

THIS INFORMATION IS DESIGNED TO FACILLITATE COMMUNICATION BETWEEN YOU AND YOUR DOCTOR. RxEOB.COM IS NOT RECOMMENDING THAT YOU CHANGE.

*FIG. 15*

HOME  DRUG LOOKUP  Rx HISTORY  HELP

CARE MANAGEMENT

MY PROFILE  RESEARCH ALTERNATIVES

SUBSCRIBERS USING DRUGS FOR DIABETES AND
ANTI-HYPERTENSIVES

| SUBSCRIBER ID | DEPENDENT NUMBER |
|---|---|
| XXX403399 | 0 |
| YYY461578 | 0 |
| WWW748540 | 0 |
| WWW463458 | 0 |
| XXX609077 | 1 |

358

HOME | DRUG LOOKUP | HELP | MY PROFILE | RESEARCH | DEPENDENTS
TERMS OF USE | PRIVACY POLICY | OUR COMMITMENT | INTERNET SECURITY | CONTACT US
© 2000-2001 RxEOB.COM, PHARMACY-FOCUSED DATA SOLUTIONS, ALL RIGHTS RESERVED.

*FIG. 17*

HOME   DRUG LOOKUP   RX HISTORY   HELP

CARE MANAGEMENT

MY PROFILE   ☐ RESEARCH ALTERNATIVES ☐

YOUR PHARMACY BENEFITS (YEAR-TO-DATE):

|  | EMPLOYER CONTRIBUTION | BENEFICIARY CONTRIBUTION | TOTAL BENEFIT EXPENSE |
|---|---|---|---|
| PAT SAMPLE | $6,087.12 | $695.00 | $6,782.12 |

PRESCRIPTION HISTORY FOR PAT SAMPLE (DEPENDENT 0)

| | DRUG NAME | DATE FILLED | COPAY | EMPLOYER COST |
|---|---|---|---|---|
| VIEW DETAIL | NEO/POLYMYXIN/HC EAR SUSP | 8/09/2000 | $5.00 | $12.39 |
| VIEW DETAIL | BENZONATATE 100MG CAPSULE | 8/04/2000 | $5.00 | $31.05 |
| VIEW DETAIL | CLARITIN 10MG TABLET | 7/29/2000 | $20.00 | $150.49 |
| VIEW DETAIL | SINGULAIR 10 MG TABLET | 6/26/2000 | $20.00 | $168.08 |
| VIEW DETAIL | HUMALOG 100U/ML VIAL | 6/26/2000 | $20.00 | $383.44 |
| VIEW DETAIL | ACCU-CHEK CMFRT CURVE STRIP | 6/26/2000 | $20.00 | $463.98 |
| VIEW DETAIL | ISOSORBIDE MN 60MG TAB SA | 6/09/2000 | $10.00 | $91.07 |
| VIEW DETAIL | FLOVENT 220MCG INHALER | 6/09/2000 | $20.00 | $446.70 |
| VIEW DETAIL | ZAROXOLYN 5MG TABLET | 6/09/2000 | $20.00 | $8.74 |
| VIEW DETAIL | CARDURA 2MG TABLET | 6/09/2000 | $20.00 | $56.88 |
| VIEW DETAIL | ZOCOR 20MG TABLET | 6/09/2000 | $20.00 | $271.89 |
| VIEW DETAIL | FUROSEMIDE 80MG TABLET | 6/09/2000 | $10.00 | $4.53 |
| VIEW DETAIL | SINGULAIR 10 MG TABLET | 4/28/2000 | $20.00 | $160.63 |
| VIEW DETAIL | HUMALOG 100U/ML VIAL | 4/22/2000 | $20.00 | $357.13 |
| VIEW DETAIL | ACCU-CHEK CMFRT CURVE STRIP | 4/22/2000 | $20.00 | $463.98 |
| VIEW DETAIL | CLARITIN 10MG TABLET | 4/17/2000 | $20.00 | $148.82 |
| VIEW DETAIL | VANCENASE AQ 84MCG SPRAY | 4/09/2000 | $50.00 | $87.55 |
| VIEW DETAIL | VANCENASE AQ 84MCG SPRAY | 3/27/2000 | $25.00 | $23.91 |
| VIEW DETAIL | VANCENASE AQ 84MCG SPRAY | 3/27/2000 | $25.00 | $23.91 |
| VIEW DETAIL | ISOSORBIDE MN 60MG TAB SA | 3/26/2000 | $10.00 | $77.58 |
| VIEW DETAIL | ZAROXOLYN 5MG TABLET | 3/24/2000 | $20.00 | $8.74 |
| VIEW DETAIL | ISOSORBIDE MN 60MG TAB SA | 3/24/2000 | $10.00 | $84.19 |
| VIEW DETAIL | FUROSEMIDE 80MG TABLET | 3/24/2000 | $10.00 | $4.53 |
| VIEW DETAIL | FLOVENT 220MCG INHALER | 3/24/2000 | $20.00 | $446.70 |
| VIEW DETAIL | ZOCOR 20MG TABLET | 3/24/2000 | $20.00 | $271.89 |
| VIEW DETAIL | MYTUSSIN AC SYRUP | 3/02/2000 | $5.00 | $.12 |
| VIEW DETAIL | GUAIFENESIN W/CODEINE SYRUP | 3/02/2000 | $5.00 | $.12 |
| VIEW DETAIL | SOD.SULFACET/SULFER LOTION | 2/18/2000 | $10.00 | $34.54 |
| VIEW DETAIL | SINGULAIR 10 MG TABLET | 2/18/2000 | $20.00 | $154.95 |
| VIEW DETAIL | BENZONATATE 100MG CAPSULE | 2/16/2000 | $5.00 | $31.30 |
| VIEW DETAIL | CLARITIN 10MG TABLET | 2/14/2000 | $20.00 | $145.54 |
| VIEW DETAIL | HUMALOG 100U/ML VIAL | 2/04/2000 | $20.00 | $357.13 |
| VIEW DETAIL | ACCU-CHEK CMFRT CURVE STRIP | 2/04/2000 | $20.00 | $463.98 |
| VIEW DETAIL | CARDURA 2MG TABLET | 2/04/2000 | $20.00 | $56.88 |
| VIEW DETAIL | SOD.SULFACET/SULFER LOTION | 1/13/2000 | $10.00 | $32.01 |
| VIEW DETAIL | SOD.SULFACET/SULFER LOTION | 1/13/2000 | $10.00 | $32.01 |

*FIG. 18*

MODEL EMPLOYER FORMULARY
DRUG UTILIZATION GROUPED BY DRUG CLASS FOR 01/01/2000 THROUGH 12/31/2001

| DRUG CLASS | PLAN PAYMENT | PLAN PERCENT OF TOTAL | RECIPIENT TOTAL | RECIPIENT % OF TOTAL |
|---|---|---|---|---|
| SELECTIVE SEROTONIN REUPTAKE INHIBITORS | $23,554.92 | 9.60% | $3,785.00 | 4.66% |
| HMG COA REDUCTASE INHIBITORS | $15,870.43 | 6.47% | $2,760.00 | 3.40% |
| OTHER ANTIHISTAMINES, NONSEDATING | $15,599.86 | 6.36% | $3,300.00 | 4.06% |
| PROTON PUMP INHIBITORS | $11,183.93 | 4.56% | $1,625.00 | 2.00% |
| SEROTONIN (5HT3) ANTAGONISTS | $9,420.76 | 3.84% | $285.00 | .35% |
| OTHER ANTIDEPRESSANTS | $9,039.88 | 3.68% | $1,419.44 | 1.74% |
| OTHER ANTIEPILEPTICS | $6,981.92 | 2.84% | $500.00 | .61% |
| CORTICOSTEROIDS | $6,562.64 | 2.67% | $3,144.34 | 3.87% |
| OTHER ANTIHISTAMINES, NONSEDATING COMBINATIONS | $6,468.44 | 2.63% | $1,920.00 | 2.36% |
| PROGESTOGENS AND ESTROGENS, SEQUENTIAL PREPARATION | $35,145.86 | 2.09% | $3,614.46 | 4.45% |

*FIG. 20*

MODEL EMPLOYER FORMULARY

EMPLOYER NAME: SAMPLE EMPLOYER 3
DRUG CLASS: CORTICOSTEROIDS

ORIGINAL DATA 380

| DRUG NAME | PLAN COST | PATIENT COST | TOTAL |
|---|---|---|---|
| BECONASE 42MCG INHALER | $23 | $15 | $38 |
| BECONASE AQ 0.042% SPRAY | $49 | $30 | $79 |
| NASOCORT NASAL INHALER | $17 | $60 | $77 |
| NASONEX 50MCG NASAL SPRAY | $31 | $60 | $91 |
| RHINOCORT NASAL INHALER | $103 | $120 | $223 |
| FLONASE 0.05% NASAL SPRAY | $192 | $90 | $282 |
| TOTALS | $417 | $375 | $792 |

MODEL DATA 382

| DRUG NAME | PLAN COST | PATIENT COST | TOTAL |
|---|---|---|---|
| BECONASE 42MCG INHALER | $23 | $15 | $38 |
| BECONASE AQ 0.042% SPRAY | $47 | $31 | $79 |
| NASOCORT NASAL INHALER | $46 | $31 | $77 |
| NASONEX 50MCG NASAL SPRAY | $54 | $36 | $91 |
| RHINOCORT NASAL INHALER | $133 | $89 | $223 |
| FLONASE 0.05% NASAL SPRAY | $169 | $112 | $282 |
| TOTALS | $475 | $317 | $792 |

CURRENT BEHAVIOR MODIFICATION HYPOTHESIS'S

THERE ARE NO CURRENT HYPOTHESIS

ADD BEHAVIOR MODIFICATION HYPOTHESIS

384

| ORIGINAL DRUG | PERCENT CHANGE | NEW DRUG |
|---|---|---|
| BECONASE 42MCG INHALER | 0 | BECONASE 42MCG INHALER |

MODEL COPAT INFORMATION

386

| PLAN THEORY | COPAY LEVEL | COPAY LEVEL | COPAY LEVEL | % |
|---|---|---|---|---|
| INITIA MIXED | 0 | 0 | 0 | 40 |

CHANGE COPAY MODEL

388

| PLAN TYPE | COPAY 1 AMOUNT | COPAY 2 AMOUNT | COPAY 3 AMOUNT | COPAY PERCENT |
|---|---|---|---|---|
| SET COPAY | 0 | 0 | 0 | 0 |

*FIG. 21*

ANTI-HYPERTENSIVES 4.5.4 ACE INHIBITORS

TIER 1
   CAPTOPRIL

TIER 2
   ACCUPRIL
   ALTACE
   CAPOTEN
   LOTENSIN
   MAVIK
   MONOPRIL
   PRINIVIL
   UNIASC

TIER 3
   VASOTEC 4.5.5 ADRENERGIC ANTAGONISTS & RELATED DRUGS

TIER 1
   CLONIDINE
   GUANFACINE
   METHYLDOPA
   PRAZOSIN
   RESERPINE

TIER 2
   ALDOMET
   CARDURA
   CATAPRES
   HYTRIN
   ISMELIN
   MINIPRESS
   TENEX

TIER 3
   CATAPRES TTS

PHARMACY BENEFITS MANAGEMENT METHOD AND APPARATUS

RELATED APPLICATION DATA

This application claims benefit of United States provisional patent application Ser. No. 60/190,556 filed on Mar. 20, 2000, the disclosure of which is incorporated herein by reference.

BACKGROUND

1. Field of the Invention

The invention relates to pharmacy benefits and more particularly to a system and method for managing pharmacy benefits to permit costs to be reduced.

2. Description of the Related Art:

Health care costs in the United States have risen dramatically over the past several decades. In 1999, health care spending accounted for 13 percent of the GDP. In the United States, most health care is delivered through employer sponsored health care plans, such as Health Maintaining Organizations (HMOs). The basic premise of an HMO is to permit the health care benefit delivered to patients, i.e. recipients, to be "managed" in order to reduce costs.

Prescription drugs are marketed and delivered in a unique manner with respect to other health care benefits. Accordingly, management, and thus cost reduction, of prescription drug benefits has historically been approached differently. Typically, Pharmacy Benefit Managers (PBMs) have been used to process claims for prescription drug benefits and attempt to control costs. PBMs ordinarily are entities that are independent of the benefit provider, e.g. an insurance company, and contract with the benefit provider to process claims for pharmacy benefits.

However, costs for prescription drugs have grown faster than any other expenditure for health care costs in recent years. In 1999 alone, spending for prescription drugs in the United States rose nearly 17 percent to $100,000,000,000.00 and is projected to continue to increase faster than any other category of health care costs over the next decade. Currently, expenditures for prescription drugs account for over 20 percent of the budget for many health care plans. It is clear that the use of PBMs, and other efforts to reduce health care spending have not been effective in reducing expenditures for prescription drug benefits.

PBMs ordinarily develop "formularies", i.e. a lists of drugs in specific classes that will be given favorable treatment. For example, the formulary may specify only a single particular drug in a class of drugs which can be prescribed under a particular pharmacy benefit plan or may classify tiers of drugs in order of preference. In some cases, the formulary directs the patient to the lowest cost drug. However, PBMs often operate under agreements with prescription drug manufacturers which include complex rebate plans. Accordingly, it is not always clear if the formulary will result in delivery of the appropriate prescription drug that is truly lowest in cost to the patient, through deductibles and copayments, and to the prescription drug benefit provider, such as an HMO.

Further, the distribution channels for prescription drugs in most cases are totally separated from the payment channels. For example, a patient may be diagnosed by a physician as having a condition that requires medication. The Physician then decides on a class of drugs appropriate for treatment of the diagnosed condition and prepares a prescription for one of plural drugs in that class. The patient then takes the prescription to a pharmacy for dispensing of the prescription drugs. If the patient has a prescription drug benefit, e.g. through health insurance coverage, the pharmacist will utilize the PBMs computer system to apply the formulary associated with that patient's benefit plan, dispense the prescribed drug, collect any deductible payment or copayment from the patient in accordance with the formulary and benefits structure of the applicable plan, and submit claims documentation to the claims processor, such as a PBM, to collect the remaining cost for the dispensed drugs.

Significantly, the patient and doctor ordinarily are not aware of the costs of the dispensed drugs and costs of alternatives thereto before, during, or after dispensing of the drugs. Further, the provider of the drug benefit, such as an employer or HMO are not aware of this information at the point of purchase either. Accordingly, prescription drugs are dispensed without consideration for direct costs. The choice amongst alternatives is made solely by the physician without knowledge of any cost effects for the patient of the benefits provider. Often the creator of the formulary has direct economic interests that may not ally with those of the patient and benefit provider. The PBM or other entity processing pharmacy benefit claims has cost information and other relevant information. However, this information often is used primarily to drive markets to profitable products and is often obfuscated by complex rebate algorithms. Such information is not available to the patient or their physician at the time of making drug therapy decisions. Therefore, costs are not always minimized for drug benefits and thus the drug benefits are not managed well.

Recent advances in communication, the Internet in particular, have facilitated on-line distribution of various information. In fact, some of the pharmacy information described above has been exchanged over the Internet. The Internet is a worldwide network of computers linked together by various hardware communication links all running a standard suite of protocols known as TCP/IP (transmission control protocol/Internet protocol). The growth of the Internet over the last several years has been explosive, fueled in the most part by the widespread use of software viewers known as browsers and HTTP (hypertext transfer protocol) which allow a simple GUI (graphical user interface) to communicate over the Internet. Browsers generally reside on the computer used to access the Internet, i.e. the client computer. HTTP is a component of TCP/IP and provides users access to files of various formats using a standard page description language known as HTML (hypertext markup language), and more recently XHTML (extensible hypertext markup language). The collection of servers on the Internet using HTTP has become known as the "World Wide Web" or simply the "Web."

Through HTML, and interactive programming protocols, the author of a particular Web page(s) is able to make information available to viewers of the Web page(s) by placing the Web page(s) on an Internet Web server in HTML format. The network path to the server is identified by a URL (Uniform Resource Locator) and, generally, any client running a Web browser can access the Web pages by the URL.

The Web has become ubiquitous in businesses and homes because it has proven to be convenient for various applications, such as news and data delivery, conducting banking and investment transactions, and the like. The Web and its authoring, transmission, and display protocols, such as browsers, HTML, CGI (common gateway interface), Active Server Pages™, and Java™, have become a worldwide standard for information exchange. However, in view of the market considerations discussed above, and other factors, the Web has not been harnessed as an effective tool in managing pharmacy benefits.

SUMMARY OF THE INVENTION

It is clear that there is a need for providing access to pharmacy cost and clinical information to patients and their physicians to permit patients and physicians to become active participants in drug therapy decisions with cost factors being considered.

A first aspect of the invention is a pharmacy benefits management system and method. A processor server has claim information relating to pharmacy benefits claims, and information relating to a claims processing formulary stored therein. A provider server has pharmacy benefits plan structure information stored therein. A management server has price information relating drugs in various classes and a processing module for correlating the claim information with the benefits plan structure information and the formulary information to identify drugs dispensed to patients, expenses associated with the drugs in accordance with the pharmacy benefits plan structure information, alternative drugs in the same class as the drugs and expenses associated with the alternative drugs.

BRIEF DESCRIPTION OF THE DRAWING

The invention will be described through a preferred embodiment and the attached Drawing in which:

FIG. 3 is a first registration screen of the preferred embodiment;

FIG. 4 is a second registration screen of the preferred embodiment;

FIG. 5 is a third registration screen of the preferred embodiment;

FIG. 6 is a fourth registration screen of the preferred embodiment;

FIG. 9 is a recipient alternative search screen of the preferred embodiment;

FIG. 10a is a recipient alternative results screen of the preferred embodiment;

FIG. 10b is another example of a recipient alternative results screen of the preferred embodiment;

FIG. 12 is a plan sponsor selection screen of the preferred embodiment;

FIG. 13 is sponsor drug utilization screen of the preferred embodiment;

FIG. 14 is sponsor drug class usage report screen of the preferred embodiment;

FIG. 15 is sponsor alternative results screen of the preferred embodiment;

FIG. 17 is a provider search results screen of the preferred embodiment;

FIG. 18 is a provider individual benefits report screen of the preferred embodiment;

FIG. 20 is a provider drug utilization report screen of the preferred embodiment;

FIG. 21 is a consultant plan alternatives screen of the preferred embodiment;

FIG. 22 is an example of a formulary for specific drug classes of the preferred embodiment.

DETAILED DESCRIPTION

Figure 1:
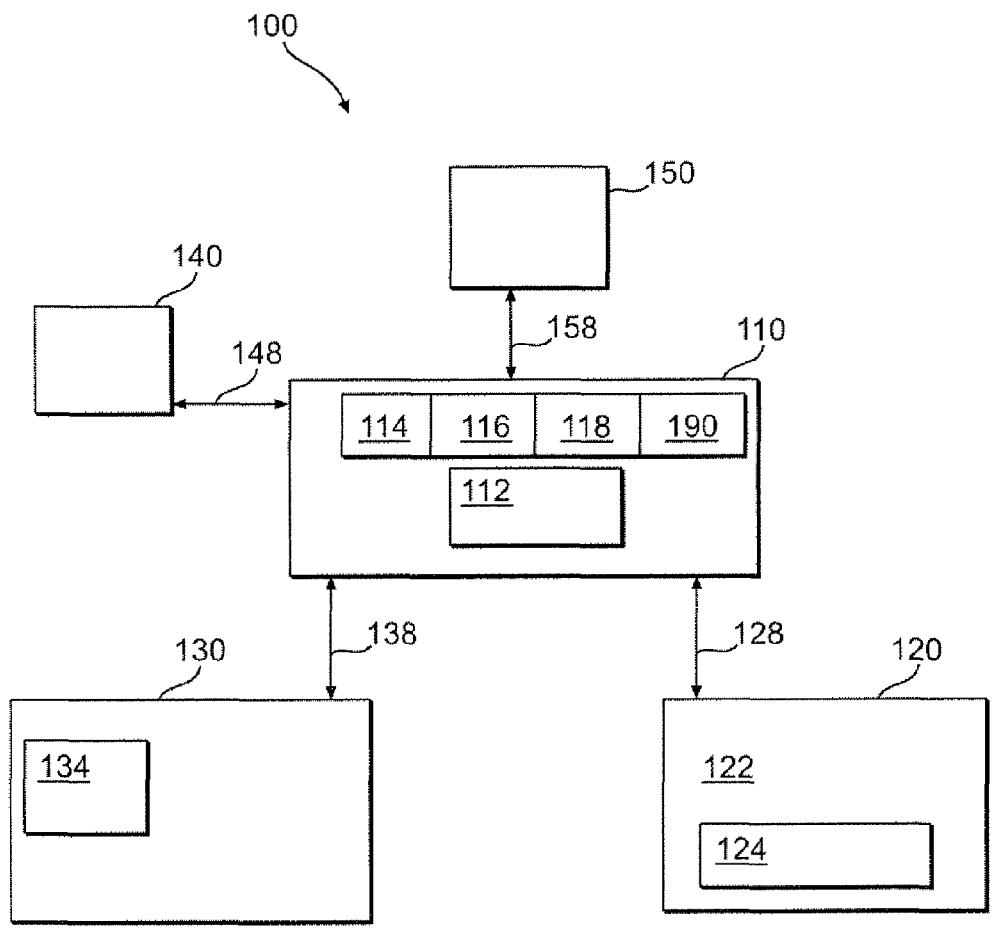
FIG. 1 is a block diagram of the computer architecture of the preferred embodiment.

FIG. 1 schematically illustrates pharmacy benefits management system 100 of the preferred embodiment. Management server 110 is a general purpose computer running an operating system and Web server software such as that distributed under the trade name APACHE™. In the preferred embodiment, management server 110 includes recipient module 114, sponsor module 116, provider module 118, and consultant module 190 as software modules constituting a processor module containing the processing logic and database capability for effecting the pharmacy benefits management functions described herein. The software modules are designated by function for the purpose of descriptive clarity herein. However, the modules need not be separate files or even separate blocks of code but can take any form of hardware and/or software for accomplishing the functionality described below. Management server 110 can also include retail cost information 112 stored therein which includes the retail costs of various drugs.

PBM server 120 is associated with a pharmacy claims processor and includes formulary information 122 specifying particular preferences of drugs in various drug classes. An example of formulary information 122 is illustrated in FIG. 22. The formulary of FIG. 22 is for a class of drugs know as Antihypertensives, including the subclasses ACE Inhibitors and Adrenic Antagonists and lists Tier 1, Tier 2, and Tier 3 drugs in each class. PBM server 120 can be a general purpose computer and is coupled to management server 110 through communications channel 128. PBM server 120 also includes benefit information 124 relating to pharmacy benefits provided to recipients, such as the type of drug dispensed, the copayment for the drug, the total cost of the drug, the identity of the pharmacy dispensing the drug, the identity of the doctor dispensing the drug, and the like.

Figure 23:
FIG. 23 is an example of a benefits structure of the preferred embodiment.

Provider server 130 is associated with a pharmacy benefits provider such as an insurance company, HMO, self insured employer, or the like. Provider server 130 can be a general purpose computer and is coupled to management server 110 through communications channel 138. Further, provider server 130 includes benefits structure information 134 indicating the pharmacy benefits provided to each recipient of the various benefits plans administered by the benefits provider. For example, benefits structure information 134 can include the deductible for pharmacy benefits to be paid by recipient prior to receiving pharmacy benefits, and the copayment for each tier of drugs to be paid by recipient. An example of benefits structure information 132 is illustrated in FIG. 23 and indicates the plan copayment for each tier of drugs in the formulary. Such a variable copayment format is referred to as a "multi-tier" plan herein.

Additionally, recipient client 140 and sponsor client 150 can be associated with a pharmacy benefit recipient (e.g. a patient, head of household, or other designee) and a plan sponsor (e.g. an employer) respectively and can be coupled to management server 110 through communication channels 148 and 158 respectively. Recipient client 140 and sponsor client 150 can each be a general purpose computer running standard client software, such as Internet browser software.

The primary functionality of recipient module 114 will be described below with reference to FIG. 2. When a pharmacy benefits recipient logs onto management server 110 through recipient client 140, recipient can access a wealth of information processed by management server 110. Of course access to information is restricted to the proper entities based on secure log in procedures and access privileges.

When using system 100 for the first time, recipient, i.e. the patient receiving a pharmacy benefit or their designee such as a parent or other guardian, accesses management server 110 through recipient client 140 and communication channel 148. Communication channel 148 can be an HTTP compliant channel, such as the Internet (including a dial up or other connection through an Internet service provider) or any other type of communication channel, such as an intranet, local are network, wide are network, or the like. Once establishing a connection between recipient client 140 and management server 110, it is determined whether recipient is registered for access to management server 110 in step 200. This determination can be made using conventional means, such as having the user select a "register" button or a "login" button, by identifying the user using cookies or the like, or in any other manner.

If recipient is registered, the procedure advances to step 210 after the recipient enters identifying information, such as a username and ID. Once again, this can be accomplished through manual entry, use of a cookie, or in any other manner. If recipient is not registered, i.e. is a first time user, the procedure goes to step 220 in which recipient enters the identity of the plan sponsor, such as recipient's employer in the case of an employer sponsored pharmacy benefits plan. FIG. 3 illustrates a screen displayed on recipient client 140 for entering the plan sponsor identity. As illustrated in FIG. 3, recipient can be prompted to enter the first several letters of the sponsor's name in field 222. After entering the first several, e.g. first two, letters of the sponsor's name, and selecting "continue" button 224, recipient is presented with the search results illustrated in FIG. 4 in which all plan sponsors corresponding to the entered letters that are part of system 100 are displayed as hypertext links in column 226 with the corresponding city of the plan sponsor in column 228.

Recipient then selects their plan sponsor from the list of search results, to determine which benefits plan the recipient is subject to, and is taken to the screen illustrated in FIG. 5 for entry of recipient personal information. For example, recipient can be prompted to enter the name of the plan subscriber in field 232 (i.e., the name of the employee or other person subscribing to the pharmacy benefits plan), pharmacy benefits plan number in field 234, recipient's name in fields 236 and 238, recipient date of birth in field 242, recipients individual coverage number in field 244, and an email address of recipient or plan subscriber in field 246. Of course, any personal information required or desired for use of system 10 can be requested and entered. Selecting button 248 causes display of the screen illustrated in FIG. 6 in which recipient is permitted to select, or change the status of, previously registered family members who can view recipient's pharmacy benefits information. For example, recipient may be a child or spouse who wishes to let their parent or spouse, or other member of the family, view their data. Accordingly, the term "recipient" as used herein refers to the person receiving the pharmacy benefit or the designee of that person for viewing pharmacy benefits information. Table 252 illustrates the current permission status of each member of recipient's family, i.e., authorized or not authorized for viewing recipient's data. Drop down menus 254 and 256 can be used to select family members and change their authorization status. Accordingly, each individual recipient has control over their own data. Preset rules regarding the legal age of consent and the like can be incorporated into the registration process to conform to current local legal standards and the like.

Figure 7:
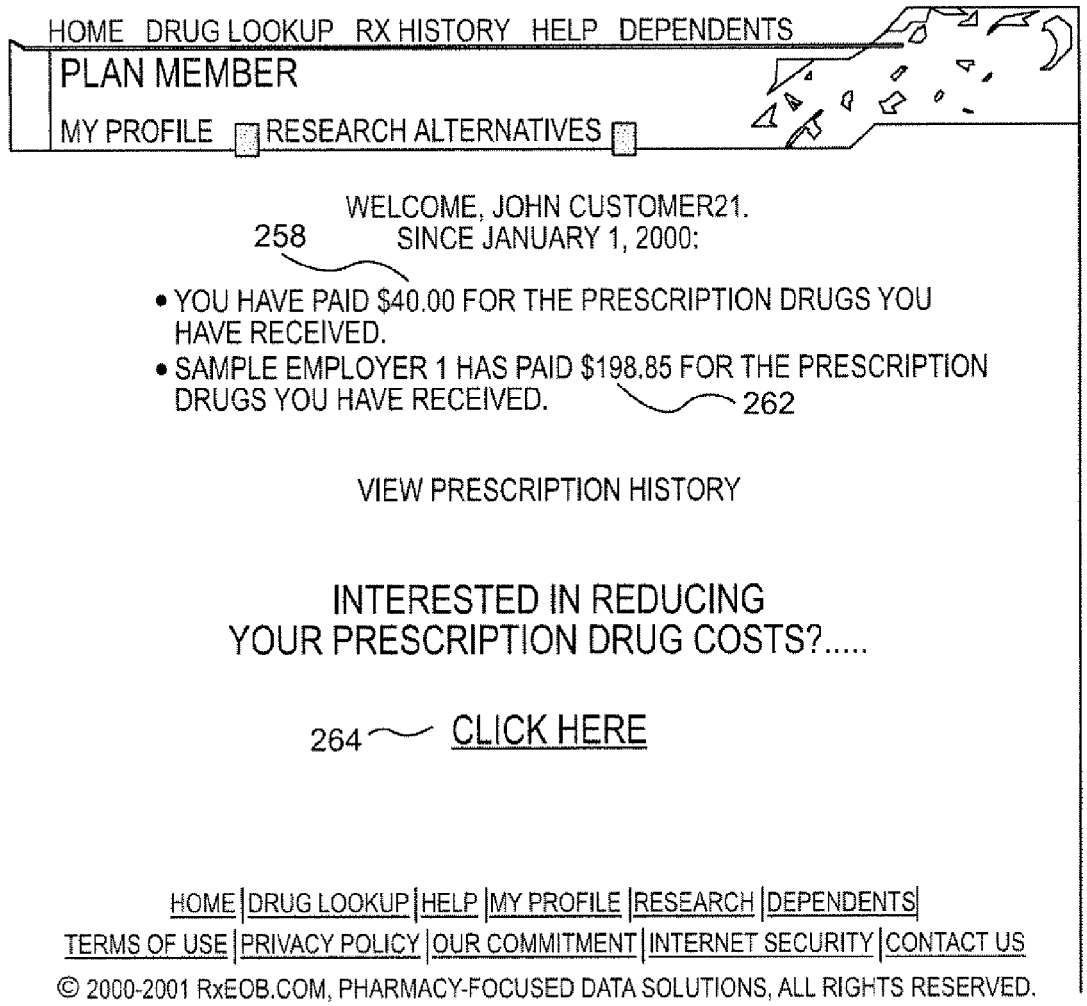
FIG. 7 is a recipient benefits summary screen of the preferred embodiment.

This completes the registration process of step 220 (FIG. 2), takes recipient to step 210 (FIG. 2), and displays the screen illustrated in FIG. 7 on recipient client 140. The screen illustrated in FIG. 7 displays a pharmacy benefits summary of recipient just registered or logged in. The summary includes out of pocket costs 258 for the appropriate time period (such as the current calendar year) and sponsor costs 262 assumed by the plan sponsor for recipient's pharmacy benefits for that same time period. This tool is the recipient's first look at the portion of the pharmacy benefit born by the plan sponsor and in and of itself is a powerful tool for managing pharmacy benefits because it raises the consciousness of recipient. The summary data is culled from data available from PBM Server 120 through communication channel 128. Communication channel 128 can be an HTTP compliant channel, such as the Internet (including a dial up or other connection through an Internet service provider) or any other type of communication channel, such as an intranet, local are network, wide are network, or the like. In particular as noted above, PBM server 120 includes benefit information 124 relating to pharmacy benefits provided to recipients, such as the type of drug dispensed, the identity of the pharmacy dispensing the drug, the identity of the doctor dispensing the drug, and the like. Also, PBM server 120 includes formulary information 122. This information can be processed by management server 110 to present out of pocket costs 258 and sponsor costs 262.

Figure 8:
FIG. 8. Is a detailed recipient benefits screen of the preferred embodiment.

Selecting button 264 will advance the procedure to step 230 in which pharmacy benefits are displayed for the time period in detail. Note that recipient can be prompted to view their own benefits or those of another family member who has authorized them to view data by selecting one of a plurality of buttons or the like. The screen illustrated in FIG. 8. provides a list of each drug dispensed to recipient (as an individual) under the pharmacy benefit plan in column 266 as well as the date of dispensing in column 272, the recipient's out of pocket costs (such as copayment) for that drug in column 274, and the plan sponsor costs in column 276. Once again, this information is culled from benefit information 124 stored in PBM server 120 and processed by management server 110 for presentation on recipient client 140. Selecting "view detail" in column 264 will provide information relating to the corresponding drug in column 266, such as the drug monograph, drug to drug interactions, and other related information that is well know and can be obtained from various sources. Pharmacy benefits from previous period, such as the last year can be accessed by selecting button 278.

System 100 has thus provided recipient with cost information to which recipient most likely never had access to before. Accordingly, recipient is more educated with respect costs of their pharmacy benefit. However, it is desirable that recipient, as a consumer, be presented with cost saving alternatives in order to close the loop in management of the pharmacy benefits provided to recipient. Accordingly, upon request by recipient, the procedure can proceed to step 240 (FIG. 2) and the screen illustrated in FIG. 9 can be displayed on recipient client 140. Drop down menu 282 permits recipient to select any one of the drugs dispensed to recipient for the purpose of comparing therapeutic alternatives. A separate drug lookup function can be provided for comparison of alternatives to drugs not dispensed pursuant to the pharmacy benefit or otherwise not on the list provided by system 100 for the recipient.

The desired quantity for comparison is entered in field 284, and the recipient selects button 286 to proceed to display of the screen illustrated in FIG. 10*a*.

In this example, recipient has selected "ACIPHEX 20 MG TABLET EC" for comparison with therapeutic alternatives and thus this drug is highlighted in column 288 which lists the alternative drugs. Column 292 displays the retail cost of each drug based on retail cost information 112 stored in management server 110. Column 294 lists the retail out of pocket costs for each drug for the recipient based on benefits structure information 132 stored in provider server 130. Column 296 lists the mail order or other alternative distribution chain out of pocket expense for each drug based on benefits structure information 132 stored in provider server 130. Of course, some pharmacy benefits plans will not include an alternative distribution option and, in such a case, column 296 can be left blank or omitted entirely. Significantly, it can be seen that the out of pocket costs for "PRILOSEC 20 MG CAPSULE DR" would have been significantly less, i.e., ten dollars as opposed to twenty-five dollars, in this example than the actual out of pocket costs for the drug that was dispensed. Of course, recipient alone cannot make the determination of which drugs to take. However, recipient can take the information presented in the screen of FIG. 10*a* to his doctor and, if the doctor agrees it is appropriate, the doctor can write a prescription for the specific medication indicated as most cost effective. Accordingly, recipient has been provided with the tools, i.e. the necessary information, to make an informed choice of medication, along with his doctor, based on price, efficacy, and safety. As an example, recipient client 140 can be a portable computer or other computer located in the doctor's office to permit decisions to be made prior to writing a prescription.

FIG. 10*b* is another example of a therapeutic alternative list generated by the preferred embodiment and has columns similar to FIG. 10*b* labeled with like reference numerals. In this example, recipient has selected "ZESTRIL 40 MG TABLET" for comparison with therapeutic alternatives and thus this drug is highlighted in column 288 which lists the alternative drugs. Column 292 displays the retail cost of each drug based on retail cost information 112 stored in management server 110. Column 294 lists the retail out of pocket costs for each drug for the recipient based on benefits structure information 132 stored in provider server 130. Column 296 lists the mail order or other alternative distribution chain out of pocket expense for each drug based on benefits structure information 132 stored in provider server 130. In this example, it can be seen that the out of pocket costs for "PRINIVIL 40 MG TABLETS" would have been significantly less, i.e., ten dollars as opposed to twenty-five dollars, than the actual out of pocket costs for ZESTRIL. Further, the total cost for PRINIVIL is also less than that for ZESTRIL. Finally, it is significant to note that these drugs are the same drug marketed under different trade names. This illustrates the anomalies associated with the use of formularies and multi-tier benefits structures and how these anomalies result in increased costs without the proper analysis and management. Once again, Recipient can take the information presented in the screen of FIG. 10*b* to his doctor and, if the doctor agrees it is appropriate, the doctor can write a prescription for the specific medication indicated as most cost effective.

Figure 11:
FIG. 11 is a recipient pharmacy benefits audit screen of the preferred embodiment.

Recipient can at any time request to conduct a pharmacy benefits audit, i.e. to examine and verify pharmacy benefits that they have received. A great deal of costs are wasted because of errors in processing claims, prescriptions never picked up by recipient and the like. Previously, a great deal of expense was incurred in attempting to recover such costs by conducting audits of a small percentage of processed pharmacy benefits claims. Of course, it is too onerous to audit all claims. By selecting the audit provision of system 100, recipient is taken to step 250 (FIG. 2) and the screen illustrated in FIG. 11 is displayed. Column 292 lists the name of each drug provided pursuant to the drug benefit and includes drop down menus for verifying whether the drug of that name was received by recipient by selection of "yes" or "no" from the menu. Column 294 lists the date each drug was dispensed by the pharmacy pursuant to the drug benefit and includes drop down menus for verifying whether the drug was received by recipient on or about that date by selection of "yes" or "no" from the menu. Column 296 lists the quantity of each drug provided pursuant to the drug benefit and includes drop down menus for verifying whether the quantity of the drug of that name was received by recipient by selection of "yes" or "no" from the menu. Column 298 lists the payment, i.e. out of pocket costs, for each drug provided pursuant to the drug benefit and includes drop down menus for verifying whether the proper payment was made by recipient. Buttons 302 and 304 can be selected for submitting recipient audit responses to management server 110 or skipping step 250 respectively. When submitted, recipient audit information can be utilized by the plan sponsor, care manager, or other parties for the purpose of auditing claims processed by the PBM or other claims processor.

Figure 2:
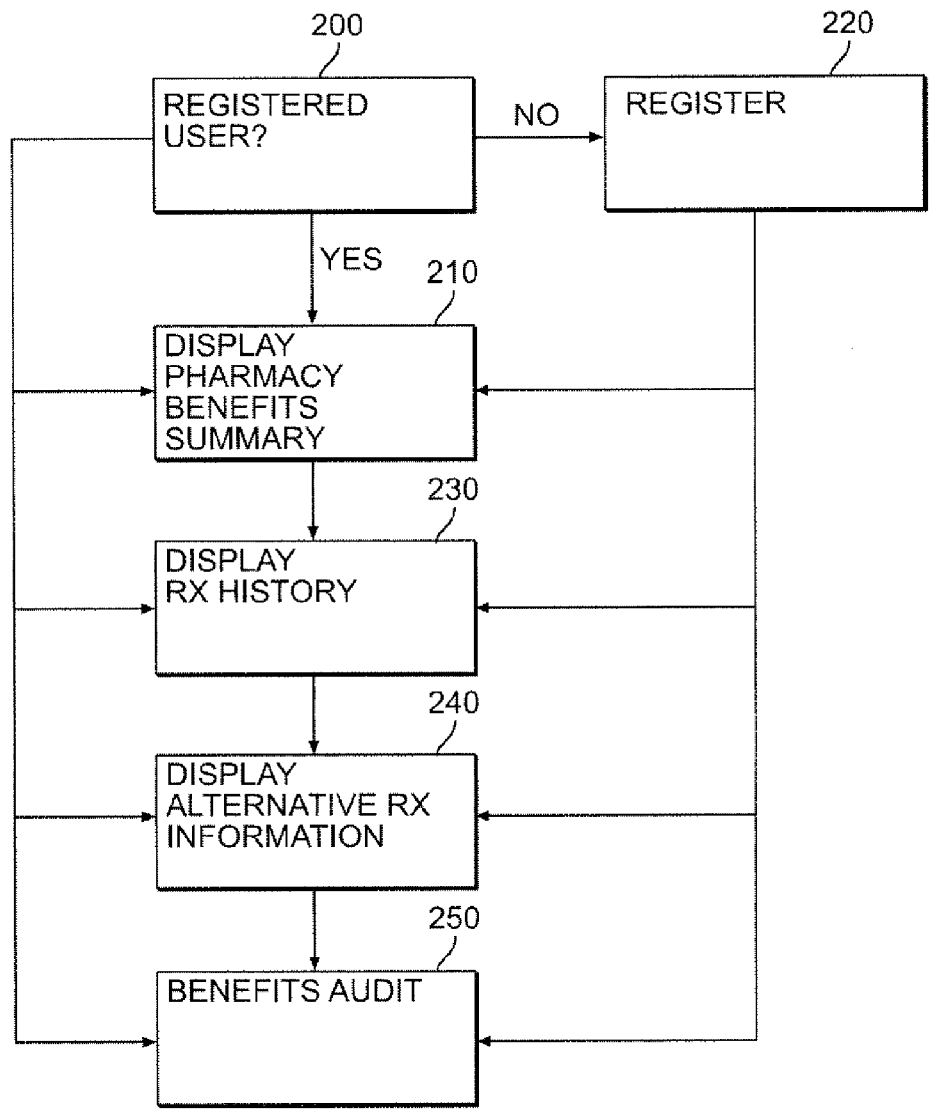
FIG. 2 is a flow chart of the function of the recipient module of the preferred embodiment.

As indicated by the arrows in FIG. 2, the various steps of recipient module 112 can be accomplished in any order and can be accomplished independently or in combination with other steps. However, ordinarily, the registration or login steps will be conducted prior to other steps.

Plan sponsor module 116 of management server 110 can be accessed by a plan sponsor, such as an employer or other entity paying for plan benefits, via sponsor client 150 and communications channel 158. Communications channel 158 can be an HTTP compliant channel, such as the Internet (including a dial up or other connection through an Internet service provider) or any other type of communication channel, such as an intranet, local area network, wide area network, or the like. Of course, as the entity paying for pharmacy benefits, plan sponsor has a great interest in controlling costs through pharmacy benefits management. However, in the case of plan sponsor being an employer, plan sponsor may not want to view, and in fact may be legally prohibited from viewing, pharmacy benefits data for individuals. For example, knowledge of the medication taken by employees could be used to discriminate against certain employees or at least create the potential appearance of such discrimination. Accordingly, plan sponsor module 114 of the preferred embodiment provides aggregate data that is useful to the plan sponsor but avoids the individual data described above with respect to recipient module 112.

After a login and/or registration procedure that can be similar to that described above with respect to recipient module 112, and which is adequate to identify plan sponsor, plan sponsor is presented with the screen illustrated in FIG. 12. Radio button 310 permits plan sponsor to select a drug utilization report aggregated by drug class. Radio buttons 312 permit selection of any one of a number of reports as indicated. Fields 306 and 308 permit the selection of relevant start and end dates respectively for any reports. If plan sponsor selects radio button 310 and selects button 314, utilization statistics are displayed on plan sponsor client 150 as illustrated in FIG. 13. The utilization statistics are grouped by drug classes as indicated in column 316 (as hypertext links). For each drug class, the statistics provide the total payment by the pharmacy plan provider for that class in column 318, the percentage of plan payment for that class as compared to total expenditures under the plan for pharmacy benefits in column 320, the total out of pocket payment for recipients for that drug class in column 322 and the percentage of out of pocket payment for that class as compared to total recipient out of pocket payment under the plan for pharmacy benefits in column 324. Of course, this information provides plan sponsor with an overview of where the pharmacy benefit expenditures are going. Further, plan sponsor can "drill down" in each drug class to obtain additional information. For example, if plan sponsor selects "selective serotonin reuptake inhibitors," The screen illustrated in FIG. 14 is displayed on sponsor client 150.

In FIG. 14, plan sponsor can view detailed information for each drug in the selected class as indicted in column 326. Specifically, sponsor can view the total payment by the pharmacy benefits plan for each brand name of a drug in column 328, the percentage of plan payment for that brand name as compared to total expenditures under the plan for the class in column 330, the total out of pocket payment for recipients for that drug in column 332 and the percentage of out of pocket payment for that drug as compared to total recipient out of pocket payment under for the class in column 324.

Plan sponsor can enter a desired quantity of any particular drug in field 336 and select button 338 to produce sponsor therapeutic alternative report as illustrated in FIG. 15. Column 336 lists the alternative drugs as hypertext links. Column 338 displays the retail cost of each drug based on retail cost information 112 stored in management server 110. Column 340 lists the out of pocket copayment for each alternative in accordance with formulary information 122 and benefits structure information 134. This tool permits sponsor to perform cost/benefit analysis for each drug based on rebate information that is available from the pharmacy benefit manager such as the PBM. For example, as seen in FIG. 14, in this example, the largest expenditures in this class were for PROZAC™. However, PROZAC™ is the third least expensive drug in the class. Possibly, rebates from the benefits manager for PROZAC™ overcome this cost differential. However, the burden can be placed on the benefits manager to demonstrate this fact. Alternatively, rebate information could be imported into system 100 and utilized to generate such an analysis automatically. Accordingly, plan sponsor has the information required to make an informed choice of benefits and can request a change in formulary by the pharmacy benefits manager, or other claims processor, with the negotiating power of the relevant information.

Figure 16:
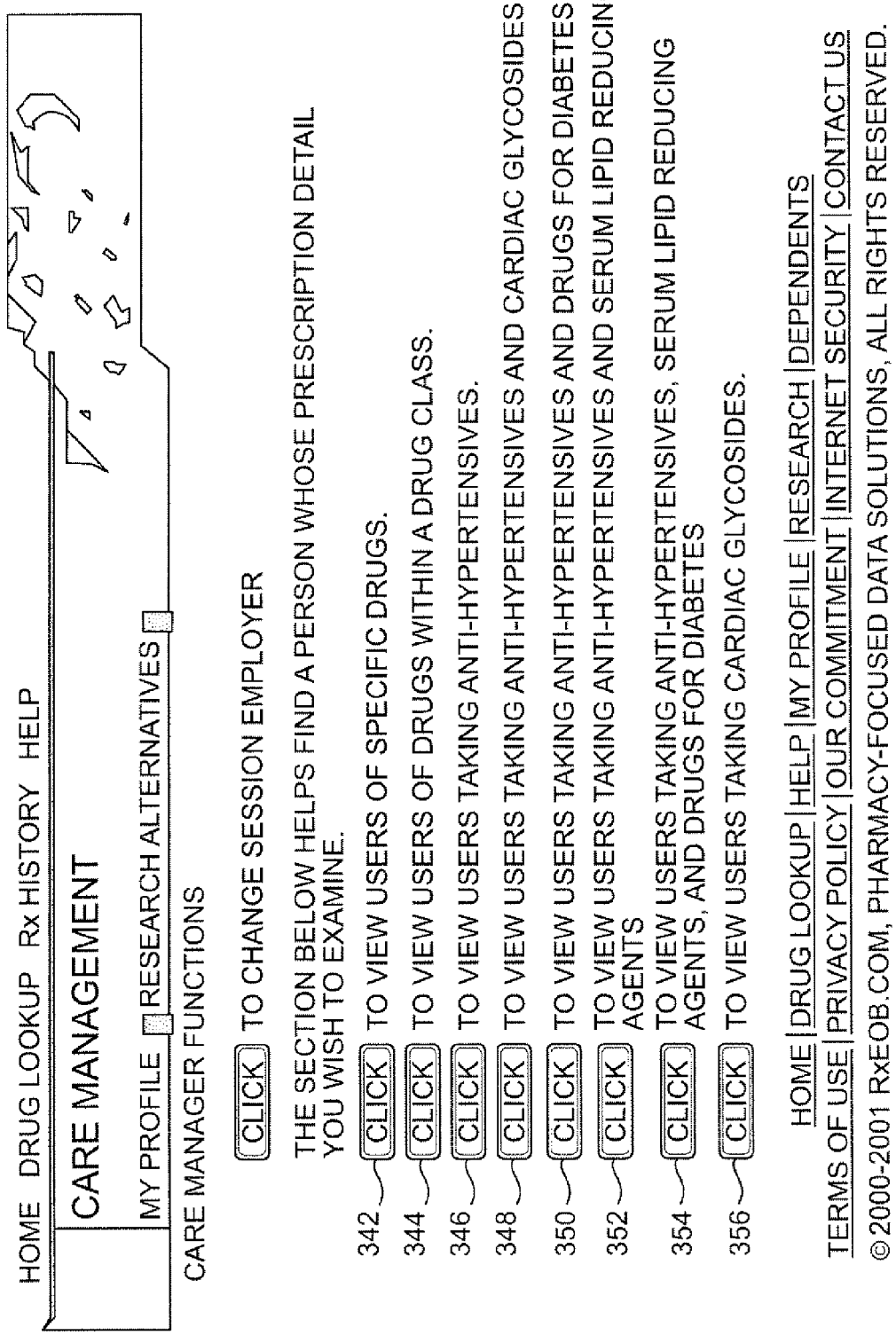
FIG. 16 is a provider search filter screen of the preferred embodiment.

Provider module 118 provides various tools designed for the benefits provider, e.g. an insurance company or HMO, is illustrated in FIG. 16. Buttons 342 through 356 correspond to predetermined search criterion as indicated. The search criterion are designed to identify patients that are at high risk for use of pharmacy benefits and thus whose care should be managed most closely. Of course, the criterion can be changed to identify any particular group of recipients. For example, if button 350 is selected, the screen illustrated in FIG. 17 is displayed on manager client 130. This screen illustrates the recipient IDs for recipients fitting the filter in column 358, i.e recipients taking anti-hypertensives and diabetes medication.

Figure 19:
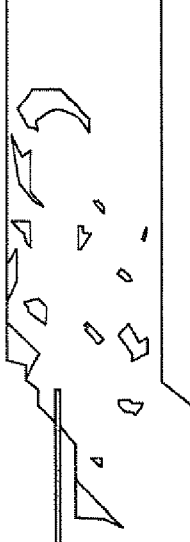
FIG. 19 is a provider prescription detail screen of the preferred embodiment.

By selecting the recipient ID, plan manager can drill down to the pharmacy benefits for that recipient, as illustrated in FIG. 18, which provides a list of each drug dispensed to recipient (as an individual) under the pharmacy benefit plan in column 360 as well as the date of dispensing in column 362, the recipient's copayment for that drug in column 364, and the plan sponsor costs in column 366. Once again, this information is culled from benefit information 124 stored in PBM server 120 and processed by management server 110 for presentation on recipient client 140. This information permits plan sponsor to police for possible adverse drug to drug interactions, use the date filled to see if the recipient is generally complying with doctor's orders, e.g. taking medication regularly when appropriate, monitor total costs to make sure recipients do not reach total benefit costs prematurely, and the like. Selecting "view detail" in column 368 will provide prescriber and pharmacy information as illustrated in FIG. 19 to permit detection of the use of plural doctors and pharmacies to obtain over doses of specific drugs and the like.

Consultant module 190 includes processing functionality that is specifically helpful to consultants in analyzing and constructing pharmacy benefit pans. Consultants using consultant module 190 can be contractors hired as consultant or in-house consultants of plan sponsor, plan provider, or another party. Accordingly, no particular party's computer is associated with consultants in the preferred embodiment. Consultant module 190 permits consultant to select a particular pharmacy benefits plan to display drug utilization of that plan by drug class as illustrated in FIG. 20. For each drug class in column 370, the statistics provide the total payment by the pharmacy benefits plan for that class in column 372, the percentage of plan payment for that class as compared to total expenditures under the plan for pharmacy benefits in column 374, the total out of pocket payment for recipients for that drug class in column 376, and the percentage of out of pocket payment for that class as compared to total recipient out of pocket payment under the plan for pharmacy benefits in column 378.

By selecting a drug class from column 370, model formularies and plan benefits can be compared for cost benefits using the screen illustrated in FIG. 21. Field 380 illustrates the sponsor cost, recipient cost and total cost for drugs in the selected drug class for the selected plan. Once again, this information is compiled from retail price information 112, formulary information 124, and benefit structure information 134. Field 382 displays plan benefits model data based on behavior hypothesis information entered by consultant as described below. In other words, field 382 presents a "what if" scenario for the entered proposed modifications. For example, in field 384, consultant can select an existing plan drug and a proposed new replacement drug (therapeutic equivalent) as well as a desired percentage of migration within the plan form the existing drug to the proposed drug. This will result in a change of total costs reflected in field 382. Similarly, in field 386, consultant can change the proposed levels of copayments or coinsurance percentage and, in field 388, the consultant can change copayment amounts of the benefits structure to see how costs are affected in field 382.

It can be seen that the preferred embodiment provides powerful tools for managing many aspects of a pharmacy benefit plan. The preferred embodiment processes information from the plan benefits structure and the plan formulary in a novel way to provide alternative costs and other information. Any type of computer architecture can be utilized in connection with the invention. The various servers and clients of the preferred embodiment can each comprise plural devices or can be consolidated with one another. Accordingly, the term "computer" as used herein refers to any device or devices capable of the disclosed processing and/or display functions. For example, the various servers and clients can be personal computers, mini computers, hand-held devices such as PDAs, thin clients, Internet appliances, or the like.

In the preferred embodiment, the communication channels are the Internet and related access links. However, the communication channels can take any form and use any appropriate protocols. For example the communication channels can be cables, wireless transmitters and receivers, optical devices. Or the like. The communication channels can be part of an intranet, LAN, WAN, or other network. All of the disclosed computers can be in a single location and the communication channels can be local busses such as serial busses, Universal serial busses, parallel busses, or the like. The various displays and data can be modified to provide the desired tools. The logic of the invention can be accomplished through any programming language, through hardwired devices, or through any other processing device. The various modules may take any form of software and/or hardware and need not be distinct form one another. The computers and other devices can have any type of memory devices for storing the desired information, such as magnetic hard drives, CD ROM drives, and the like. Of course, the computers can have any appropriate display devices and data input devices and can use any appropriate user interface. Of course, a display can be a CRT, LCD, printer, or any other device capable of presenting information. The various information can be downloaded in any manner such as through a database query, a file transfer, or the like and thus the term "download" as used herein refers broadly to any transfer of data and can be accomplished in real time, or in advance of when the data is needed.

The invention has been described through a preferred embodiment, however various modifications can be made without departing from the scope of the invention as defined by the appended claims and legal equivalents thereof.

What is claimed is:

1. A pharmacy benefits management system comprising:
   pharmacy benefits means for receiving claim information relating to pharmacy benefits claims processed by a claims processing facility, said claim information including identification of drugs dispensed to individual patients;
   management means for receiving pharmacy benefits formulary information and price information relating to drugs in various classes;
   provider means for receiving pharmacy benefits plan structure information including deductible information and co-payment information stored therein to determine a recipient's prescription benefit plan and identify the subscriber of the prescription benefit plan;
   said management means further;
      calculates out-of-pocket costs, sponsor costs, and total costs of the drugs dispensed to patients based upon the determined prescription benefit plan, the identified subscriber, the received claim information, the received formulary information, the received pharmacy benefits plan structure, and the received price information;
      aggregates the out-of-pocket costs, sponsor costs, and total costs of the drugs dispensed to patients based upon at least one of identity of drug dispensed, type of drug dispensed, formulary information, identity of pharmacy dispensing drug, and identity of doctor prescribing drug; and
      transmits the aggregated out-of-pocket costs and sponsor costs to the recipient of prescription benefits.

2. The system recited in claim 1, wherein the identified drugs dispensed to a patient also indicate the date the drugs were dispensed.

3. The system recited in claim 1, wherein the management means further calculates out-of-pocket costs, sponsor costs, and total costs of alternative drugs, wherein the alternative drugs are therapeutic alternatives with respect to the drugs dispensed to patients.

4. The system recited in claim 3, wherein said management means further:
   calculates out-of-pocket costs, sponsor costs, and total costs of the drugs dispensed to patients and the alternative drugs in an alternative pharmacy, wherein the alternative pharmacy is an alternative distribution chain capable of supplying the drugs dispensed to patients and the alternative drugs; and
   aggregates out-of-pocket-costs, sponsor costs and total costs of the drugs dispensed to patients and the alternative drugs based upon the identity of the alternative distribution chain.

5. The system recited in claim 1, wherein the benefits plan structure information received from the provider means and the formulary information received from the management means relate to a multi-tier benefits plan.

6. The system recited in claim 5, wherein the out-of-pocket costs, sponsor costs, and total costs associated with the drugs dispensed to patients and the out-of-pocket costs, sponsor costs, and total costs associated with the alternative drugs includes copayment information, sponsor information, and total cost information.

7. The system recited in claim 1, wherein said management means further:
   calculates out-of-pocket costs, sponsor costs, and total costs of the drugs dispensed to patients in an alternative pharmacy, wherein the alternative pharmacy is an alternative distribution chain capable of supplying the drugs dispensed to patients; and
   aggregates out-of-pocket-costs, sponsor costs and total costs of the drugs based upon the identity of the alternative distribution chain.

8. The system recited in claim 1 further comprising means for entering proposed changes to any of the claim information, the benefit plan structure information, and the formulary information and displaying model data based on the proposed changes.

9. The system recited in claim 8, wherein the proposed changes comprise any of changes to copayment amounts, changes to copayment levels, and changes drugs dispensed.

10. The system recited in claim 1, further comprising a second pharmacy benefits means for receiving a second set of claim information, the second set of claim information relating to pharmacy benefits claims processed by a second claims processing facility, and the second set of claim information including identification of drugs dispensed to patients.

11. The system recited in claim 10, wherein said management means further calculates out-of-pocket costs, sponsor costs, and total costs of alternative drugs ,wherein the alternative drugs are therapeutic alternatives with respect to the drugs dispensed to patients.

12. The system recited in claim 11, wherein said management means further calculates out-of-pocket costs, sponsor costs, and total costs of the drugs dispensed to patients and the alternative drugs in an alternative pharmacy, wherein the alternative pharmacy is an alternative distribution chain capable of supplying the drugs dispensed to patients and the alternative drugs; and
   said management means further aggregates out-of-pocket-costs, sponsor costs and total costs of the drugs dispensed to patients and the alternative drugs based upon the identity of the alternative distribution chain.

13. A pharmacy benefits management method comprising the steps of:

receiving claim information from a pharmacy benefits server, the claim information relating to pharmacy benefits claims processed by a claims processing facility, said claim information including identification of drugs dispensed to individual patients;

receiving pharmacy benefits formulary information from the pharmacy benefits server;

receiving pharmacy benefits plan structure information from a provider server, the pharmacy benefits plan structure including deductible information and co-payment information;

receiving price information from a management server, the price information relating to drugs in various classes;

determining a recipient's prescription benefit plan;

identifying a subscriber of the recipient's prescription benefit plan;

calculating, by the management server, out-of-pocket costs, sponsor costs, and total costs of the drugs dispensed to patients based upon the determined prescription benefit plan, the identified subscriber, the received claim information, the received formulary information, the received pharmacy benefits plan structure, and the received price information;

aggregating, by the management server, the out-of-pocket costs, sponsor costs, and total costs of the drugs dispensed to patients based upon at least one of identity of drug dispensed, type of drug dispensed, formulary information, identity of pharmacy dispensing drug, and identity of doctor prescribing drug; and transmitting the aggregate out-of-pocket costs and sponsor costs to the recipient of prescription benefits.

14. A method as recited in claim 13, wherein the drugs dispensed to patients in said calculating step are drugs previously dispensed to a patient indicated by the date the selected drugs were dispensed.

15. A method as recited in claim 13, wherein the calculating step includes calculating out-of-pocket costs, sponsor costs, and total costs of alternative drugs, wherein the alternative drugs are therapeutic alternatives with respect to the drugs dispensed to patients.

16. A method as recited in claim 15, wherein
the calculating step includes calculating out-of-pocket costs, sponsor costs, and total costs of the drugs dispensed to patients and the alternative drugs in an alternative pharmacy, wherein the alternative pharmacy is an alternative distribution chain capable of supplying the drugs dispensed to patients and the alternative drugs, and the aggregating step includes aggregating out-of-pocket-costs, sponsor costs and total costs of the drugs dispensed to patients and the alternative drugs based upon the identity of the alternative distribution chain.

17. A method as recited in claim 13, wherein the benefits plan structure information and the formulary information relate to a multi-tier benefits plan.

18. A method as recited in claim 17, wherein the out-of-pocket costs, sponsor costs, and total costs associated with the drugs dispensed to patients and the out-of-pocket costs, sponsor costs, and total costs associated with the alternative drugs includes copayment information, sponsor information, and total cost information.

19. A method as recited in claim 13, wherein;
the calculating step includes calculating out-of-pocket costs, sponsor costs, and total costs of the drugs dispensed to patients in an alternative pharmacy, wherein the alternative pharmacy is an alternative distribution chain capable of supplying the drugs dispensed to patients; and the aggregating step includes aggregating out-of-pocket-costs, sponsor costs and total costs of the drugs based upon the identity of the alternative distribution chain.

20. A method as recited in claim 13 further comprising:
entering proposed changes to any of the claim information, the benefit plan structure information, and the formulary information; and displaying model data based on the proposed changes.

21. A method as recited in claim 20, wherein the proposed changes comprise any of changes to copayment amounts, changes to copayment levels, and changes to drugs dispensed.

22. The method recited in claim 13, further comprising displaying aggregate out-of-pocket costs and sponsor costs to the sponsor of prescription benefits.

23. The method recited in claim 13, further comprising receiving a second set of claim information from a second pharmacy benefits server, the second set of claim information relating to pharmacy benefits claims processed by a second claims processing facility, and the second set of claim information including identification of drugs dispensed to patients.

24. The method recited in claim 23, wherein the calculating step includes calculating out-of-pocket costs, sponsor costs, and total costs of alternative drugs ,wherein the alternative drugs are therapeutic alternatives with respect to the drugs dispensed to patients.

25. The method recited in claim 24, wherein the calculating step includes calculating out-of-pocket costs, sponsor costs, and total costs of the drugs dispensed to patients and the alternative drugs in an alternative pharmacy, wherein the alternative pharmacy is an alternative distribution chain capable of supplying the drugs dispensed to patients and the alternative drugs; and the aggregating step includes aggregating out-of-pocket-costs, sponsor costs and total costs of the drugs dispensed to patients and the alternative drugs based upon the identity of the alternative distribution chain.

* * * * *